United States Patent
Kall

(10) Patent No.: US 8,792,952 B2
(45) Date of Patent: Jul. 29, 2014

(54) SENSOR HOLDER TO BE APPLIED ON AN APPENDAGE OF A SUBJECT

(75) Inventor: Magnus Kall, Espoo (FI)

(73) Assignee: General Elecric Company, Schenectady, NY (US)

(*) Notice: Subject to any disclaimer, the term of this patent is extended or adjusted under 35 U.S.C. 154(b) by 1 day.

(21) Appl. No.: 13/528,503

(22) Filed: Jun. 20, 2012

(65) Prior Publication Data
US 2013/0345528 A1 Dec. 26, 2013

(51) Int. Cl.
*A61B 5/1455* (2006.01)

(52) U.S. Cl.
USPC ............................ 600/344; 600/310; 600/323

(58) Field of Classification Search
USPC .................................................. 600/309–344
See application file for complete search history.

(56) References Cited

U.S. PATENT DOCUMENTS

| 5,035,243 | A * | 7/1991 | Muz .............................. 600/344 |
| 6,745,061 | B1 | 6/2004 | Hicks et al. |
| 2006/0106294 | A1 | 5/2006 | Maser et al. |
| 2007/0032708 | A1 | 2/2007 | Eghbal et al. |
| 2011/0124995 | A1 | 5/2011 | Karma et al. |

FOREIGN PATENT DOCUMENTS

DE 20 2005 017 567 U1 4/2007

* cited by examiner

*Primary Examiner* — Eric Winakur
*Assistant Examiner* — Marjan Fardanesh

(57) ABSTRACT

A sensor holder to be applied on an appendage of a subject is disclosed herein. The sensor holder includes a substrate with at least a first location for a first sensor component, the substrate surrounding a hollow for receiving the appendage along a longitudinal axis of the hollow. The substrate is gradually thickening when drawing away at least a predetermined distance from the at least first location for the first sensor component along a perpendicular direction of the substrate in relation to the longitudinal axis of the hollow.

20 Claims, 4 Drawing Sheets

_US 8,792,952 B2_

SENSOR HOLDER TO BE APPLIED ON AN APPENDAGE OF A SUBJECT

BACKGROUND OF THE INVENTION

This disclosure generally relates to a sensor holder to be applied on an appendage of a subject. The sensor holder comprises a substrate with at least a first location for a first sensor component. The substrate surrounds a hollow for receiving the appendage along a longitudinal axis of the hollow.

The concentration of substances, such as oxygen, in tissue is typically measured non-invasively by measuring the absorption of light at different wavelengths in the tissue. By calculating the ratio of absorption for different wavelengths, the concentration of a substance can be calculated, e.g. absorption ratio of red and infrared light is used to determine the concentration of oxygenated blood. Typically, what is measured is the color of the tissue. In the case of oxygenation, the tissue becomes darker red at lower saturations and brighter red at higher saturations. The different colors of the tissue absorb light of different wavelengths (color) differently, and by measuring these absorptions, the relative concentration can be calculated. By measuring more or other wavelength absorptions, more substance concentrations can be calculated in the same manner. The light is typically emitted using light emitting diodes (LED's) of different wavelengths and detected using a photodetector (e.g. photodiode).

In a typical implementation, the LED's of different wavelength are lit up in sequence, making it possible to measure the absorption of each wavelength using a single photodetector which is sensitive over a wide wavelength range. Short pulses are typically used to maximize optical output power while limiting the total power to prevent heating of the optical components. Typical wavelengths used for $SpO_2$ measurement are 650 . . . 670 nm for red and 880 . . . 950 nm for infrared.

Semiconductive light emitting diodes (LED's) are typically used as light sources for SpO2 sensors. The LED's used in $SpO_2$ sensors today are manufactured on a wafer and diced into small chips that are mounted on a substrate. The typical manufacturing process involves bonding the chip to a substrate using a conductive adhesive, curing the adhesive in an oven, bonding a gold wire from the top of the chip to a contact pad on the substrate and finally encapsulating the whole assembly in a clear encapsulant. To be able to utilize this assembly in an $SpO_2$ sensor, it must further be connected to electrical conductors connecting the LED electrodes to an $SpO_2$ monitor. This is typically done using soldering or wire welding.

There are generally two types of sensors used for this purpose, reusable and disposable. The reusable sensors are typically clip-on sensors that use a spring force to keep the sensor on the patient or alternatively there is an additional accessory for applying the sensor to the patient. Disposable sensors are typically adhesive and are adhered to or wrapped around the area of the patient where the measurement is done. Common for both sensor types is that they apply pressure on the sensor site and cover the patient's skin. Adhesives are also known to cause skin reactions especially during prolonged use. To mitigate potential side-effects of this, such as pressure necrosis or skin symptoms, manufacturers typically recommend switching the sensor site every few hours. With reusable sensors, this is easily accomplished, but with adhesive disposable sensors, the performance of the adhesive degrades with each removal and there is typically adhesive residue at the former sensor site.

BRIEF DESCRIPTION OF THE INVENTION

The above-mentioned shortcomings, disadvantages and problems are addressed herein which will be understood by reading and understanding the following specification.

In an embodiment, a sensor holder to be applied on an appendage of a subject includes a substrate with at least a first location for a first sensor component, the substrate surrounding a hollow for receiving the appendage along a longitudinal axis of the hollow. The substrate is configured to become gradually thicker when drawing away at least a predetermined distance from the at least first location for the first sensor component along a perpendicular direction of the substrate in relation to the longitudinal axis of the hollow.

In another embodiment, a sensor holder to be applied on an appendage of a subject includes a substrate having opposite portions, which are a first substrate portion and a second substrate portion, with a first location on/in the first substrate portion for a first sensor component for emitting radiation and with a second location on/in the second substrate portion for a second sensor component for receiving the radiation emitted by the first sensor component, the substrate surrounding a hollow for receiving the appendage along a longitudinal axis of the hollow. The first and second substrate portions are configured to become gradually thicker when drawing away at least a predetermined distance from the first location for the first sensor component and from the second location for the second sensor component along a perpendicular direction of the substrate in relation to the longitudinal axis of the hollow.

In yet another embodiment, a sensor holder to be applied on an appendage of a subject includes a substrate having four portions, which are a first substrate portion opposite to a second substrate portion and a third substrate portion opposite to a fourth substrate portion, with a first location on/in the first substrate portion for a first sensor component for emitting radiation and with a second location on/in the second substrate portion for a second sensor component for receiving the radiation emitted by the first sensor component, the substrate surrounding a hollow for receiving the appendage along a longitudinal axis of the hollow. The first and second substrate portions are configured to become gradually thicker when drawing away at least a predetermined distance from the first location for the first sensor component and from the second location for the second sensor component along a perpendicular direction of the substrate in relation to the longitudinal axis of the hollow, and that a thickness of the third and fourth substrate portions is substantially uniform.

Various other features, objects, and advantages of the invention will be made apparent to those skilled in art from the accompanying drawings and detailed description thereof.

DETAILED DESCRIPTION OF THE INVENTION

Specific embodiments are explained in the following detailed description making a reference to accompanying drawings. These detailed embodiments can naturally be modified and should not limit the scope of the invention as set forth in the claims.

Figure 1:
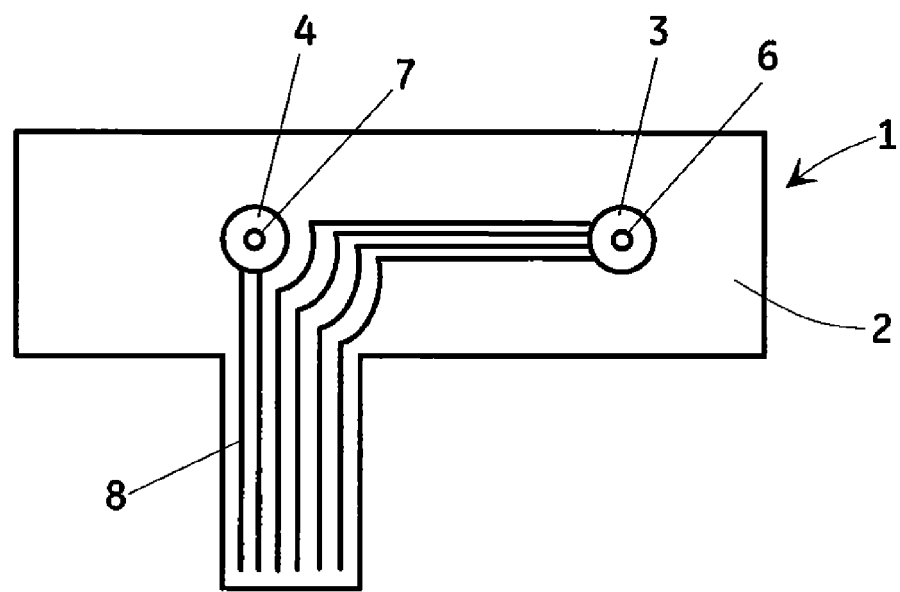
FIG. 1 is a schematic view of a sensor holder in planar form with printed conductors and sensor components in accordance with an embodiment.
Figure 2:
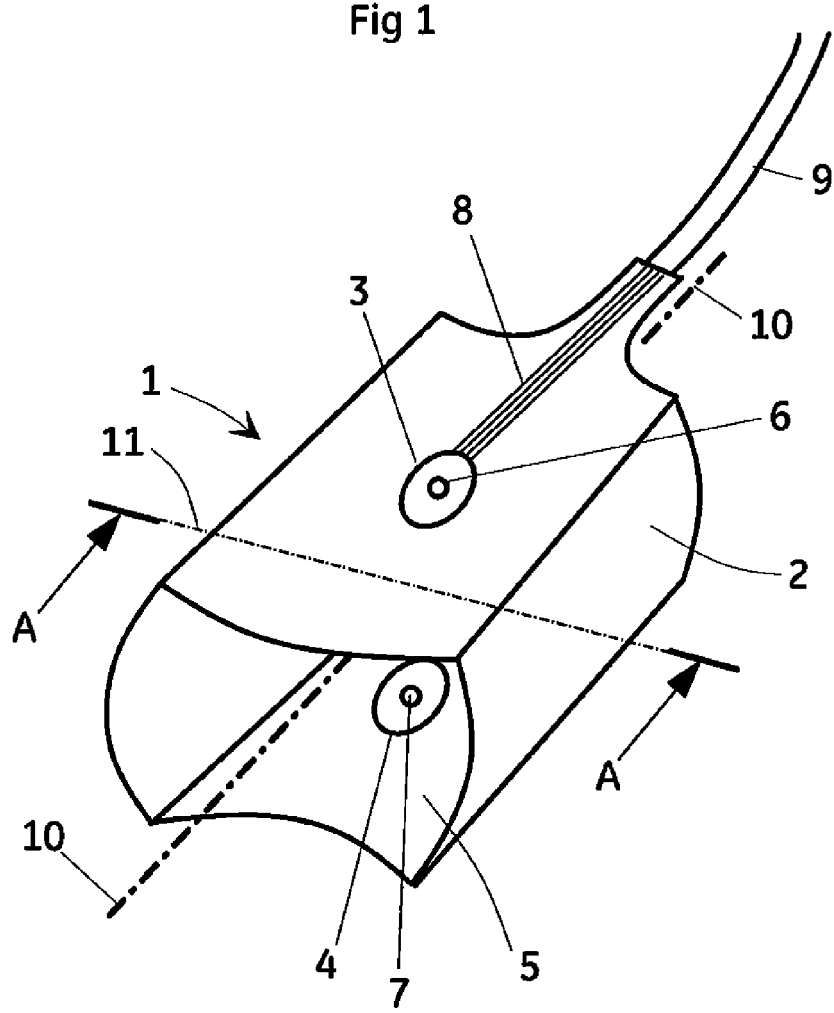
FIG. 2 is a perspective top view of a sensor holder when opposite ends of the sensor holder of FIG. 1 are joined to form a closed loop cross section with a hollow for an appendage inside the sensor holder.

The sensor holder in accordance with an embodiment may be disposable that has the benefits of a reusable sensor holder with regards to repositionability but may still be low cost and manufactured from disposable materials. FIG. 1 shows a schematic representation of the sensor holder 1 to be applied on an appendage of a subject in accordance with an embodiment. In this Figure the sensor holder is opened out into a planar form. The sensor holder comprises a substrate 2 and at least a first location 3 for a first sensor component 6, which component may be part of a sensor or the sensor in its entirety, such as a medical sensor, but in this specific embodiment there is a second location 4 for a second sensor component 7, which locations and sensor components are opposite each other when opposite ends the substrate 2 of the sensor holder 1 are joined as shown in FIG. 2, in which case the substrate surrounds a hollow 5 receiving the appendage of the subject, such as a finger or toe, along a longitudinal axis 10 of the hollow. The first sensor component 6 of the first location 3 in this specific embodiment may be an emitter emitting an electromagnetic radiation and the second sensor component 7 in the second location 4 may be a detector receiving the electromagnetic radiation emitted by the emitter. Both in FIGS. 1 and 2 there are conductors 8 connected to drive and measurement electronics (not shown in Figures) which is typically outside the sensor holder in a monitor (not shown in Figures). The conductors 8 may be for example printed conductors or wires. The conductors 8 which are conductive traces can be printed on a substrate 2 connecting the first sensor component 6 and the second sensor component 7 electrically to a connection point (not shown in Figure) which can be terminated to a connector (not shown in Figures) or a cable 9 as shown in FIG. 2. Also the first and second sensor components can be printed on the substrate. It is also possible that the conductors 8 are wires and the first and second sensor components are discrete components assembled into the sensor holder.

Figure 3:
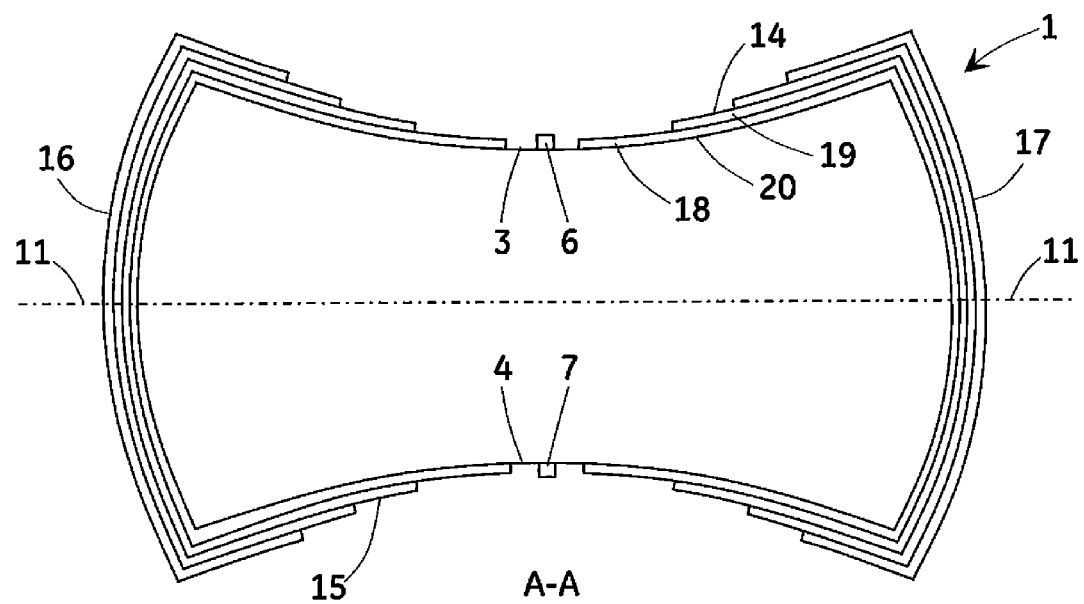
FIG. 3 is a cross section of the sensor holder of FIG. 2 taken along lines A-A in accordance with an embodiment.

FIG. 3, which is a cross section of the sensor holder of FIG. 2 taken along lines A-A, shows in more detailed the structure of the substrate 2 and the operating principle of the sensor holder 1. The substrate comprises opposite substrate portions, which are a first portion 14 having the first location 3 for the first sensor component 6 and a second portion 15 having the second location 4 for the second sensor component 7. The first and second substrate portions may be concave. Further the substrate may comprise two other substrate portions, which are a third portion 16 and a fourth portion 17, which are opposite each other and which are between or connect the first and second substrate portions. The third and fourth substrate portions may be convex. Thus the portions are joined together in sequence first 14, third 16, second 15, fourth 17 and first 14 forming a closed loop.

The substrate in FIG. 3 becomes gradually thicker when drawing away at least a predetermined distance from the at least first location 3 for the sensor along a perpendicular direction 11 of the substrate in relation to the longitudinal axis 10 of the hollow 5. At least a first substrate portion 14 having the first location 3 for the first sensor component 6 is gradually thickening. Typically the substrate is gradually thickening when drawing sideways away from the at least first location 3 along both substantially opposite directions perpendicular in relation to the longitudinal axis 10 of the hollow. It may be advantageous to make a second substrate portion 15 also gradually thickening along a perpendicular direction 11 of the substrate in relation to the longitudinal axis 10 of the hollow 5 irrespective of whether or not there is the second location 4 for the second sensor component 7. The first and/or second locations for the sensor components may be in or on the respective substrate portions. Thus the thickness of the first portion 14 and possibly the second portion 15 is decreasing towards the location 3 for the sensor component along a perpendicular direction of the substrate 2 in relation to the longitudinal axis 10 of the hollow 5. By varying the thickness of the first substrate portion 14 and the second substrate portion 15, the spring force of the sensor holder 1 can be tuned for different patient populations or optimized for the widest possible patient range. The thickness of the third portion 16 and the fourth portion 17, which portions are opposite each other, can be substantially uniform or monotonous.

Figure 4:
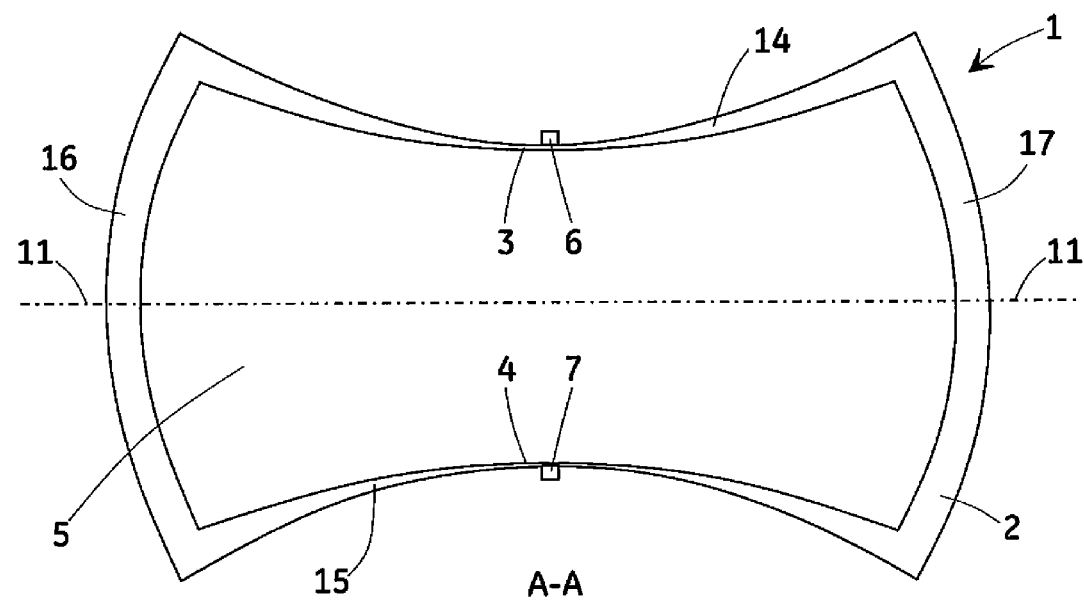
FIG. 4 is a cross section of the sensor holder of FIG. 2 taken along lines A-A in accordance with another embodiment.
Figure 6:
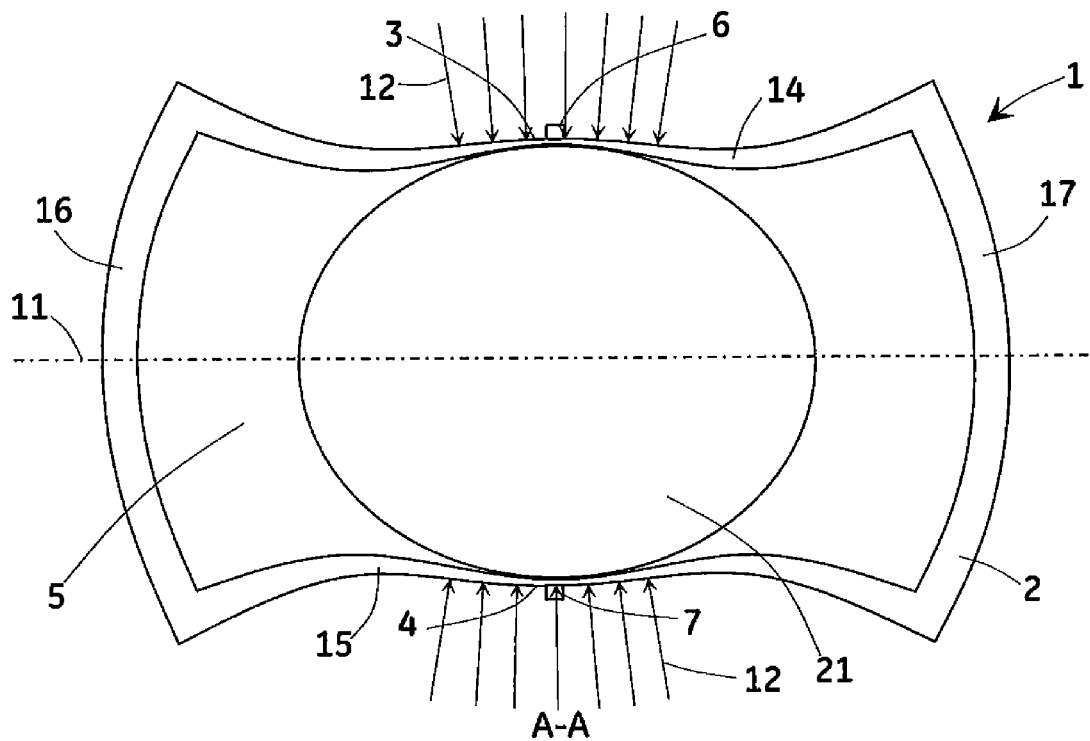
FIG. 6 is the sensor holder of FIG. 5, when the pressure on the opposite portions of the sensor holder has been released and the sensor holder has conformed around the appendage.

The gradual thickening may be stepwise as shown in FIG. 3 or continuous as shown in FIG. 4 towards or even until the third and fourth substrate portions. The continuously thickening material can be manufactured in a single-phase manufacturing process by varying the thickness of the material during the extrusion process. This may require a custom extrusion, but results in a simpler assembly with a lower number of parts and process steps. The stepwise thickening portion can be manufactured by fixing layers, at least two different layers, one on top of the other resulting in a variable thickness multilayer structure, which can be also considered a sandwich structure. A first layer 18 may extend away from the location 3 for the medical sensor 6, and a second layer 19 fixed on top of the first layer 18 extends away from a predetermined distance from the location 3 for the medical sensor 6 along a perpendicular direction of the substrate in relation to the longitudinal axis of the hollow. In case there are other layers fixed on top of the previous layer, at least most of them extend from further away than the previous layer from the location 3 along a perpendicular direction of the substrate 2 in relation to the longitudinal axis 10 of the hollow 5. Thus the substrate may comprise several layers at least partly overlapping and which layers are fixed directly or indirectly on top of the first layer 18. A bottom layer 20 may be bordering the hollow and the first layer may be on top of the bottom layer. The bottom layer between the first layer 25 and the hollow 5, may be for example a thin polyester sheet which can comprise conductive and graphic printing. The stiffer top polycarbonate layers provide the stiffness needed to form the sensor holder structure and provide the desired surface pressure 12 profile on the appendage. Other suitable materials for substrate may also be used. FIG. 6 also show how the gradually changing thickness of the sensor holder results in an even surface pressure 12 on the appendage, which offers comprehensive optical coverage, in case the sensor component comprises an optical component, and low, evenly distributed surface pressure 12.

Figure 5:
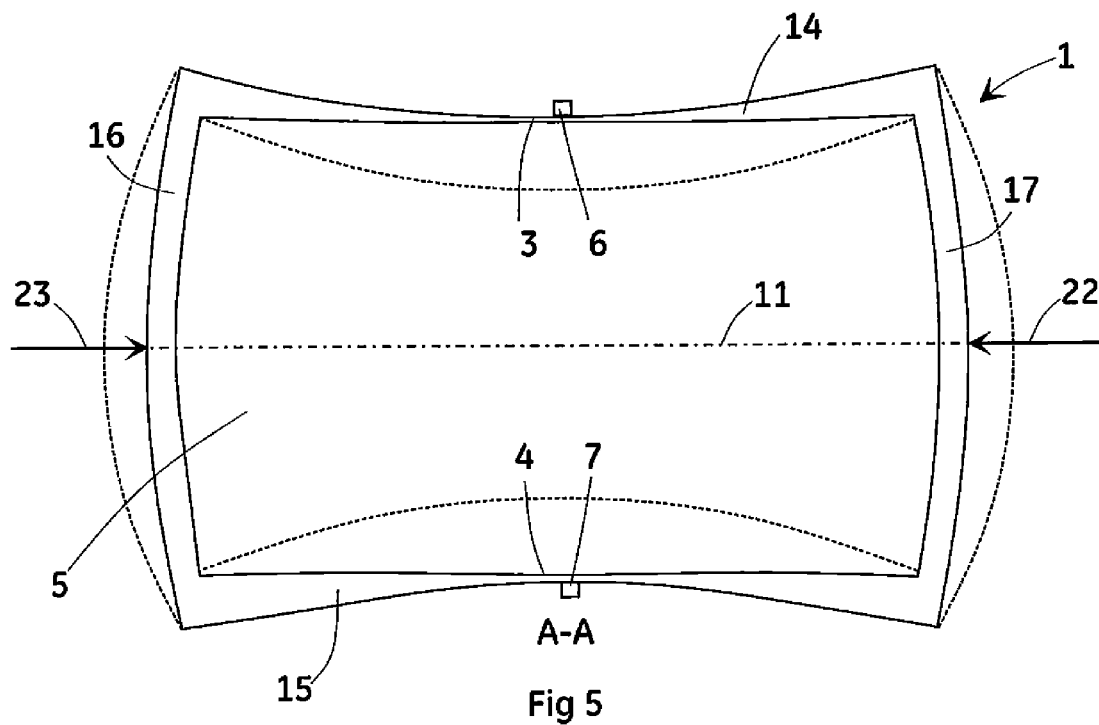
FIG. 5 is the sensor holder of FIG. 4, when the pressure is applied to opposite portions of the sensor holder.

FIGS. 3, 4, 5 and 6 show the operating principle of applying the sensor holder to the appendage 21, which is in this case a finger. In FIGS. 3 and 4 the sensor assembly is in a relaxed state. In FIG. 5, pressure as shown by arrows 22 and 23 is applied to the third substrate portion 16 and the fourth substrate portion 17 to deform them. The pressure applied to the third substrate portion 16 and the fourth substrate portion 17 is increasing the opening of the hollow 5 in the sensor holder, allowing the appendage 21 to be inserted. FIG. 6 shows how the sensor holder conforms around the appendage when the pressure on the third substrate portion 16 and the fourth substrate portion 17 is released. While on the appendage, the sensor holder remains elastically deformed, which results in a pressure distribution 12 on the appendage around the first sensor component 6 and the second sensor component 7 areas.

Figure 7:
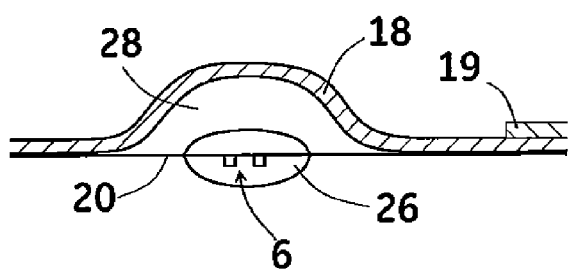
FIG. 7 is a partial view of the sensor holder of FIG. 2 showing a location for a sensor component in accordance with an embodiment.

FIGS. 7, 8, 9 and 10 show several alternatives for how to attach the first sensor component 6 to the first location 3 for the sensor holder or the substrate 2. The first sensor component can comprise for instance several light emitting diodes. Correspondingly the second sensor component 7 can be attached to the second location 4 of the sensor holder or the substrate 2, which second location may be for instance opposite the first location for the first sensor component. The first sensor component can be attached for instance on one side of the bottom layer 20. FIG. 7 shows an attachment method and construction where the first sensor component is attached directly on the bottom layer 20, such as an elastic polyester sheet, and is then encapsulated using an optically clear material to form a lens 26 over the first sensor component 6, such as an emitter comprising optics. The first layer 18, such as a stiffer polycarbonate layer, on top of the bottom layer away from the hollow 5 has a recess 28 over the lens 26 to allow the lens to move and conform to the surface structure of the skin under the lens. Here the bottom layer 20 acts as a spring to allow the lens to align itself with the skin surface.

Figure 8:
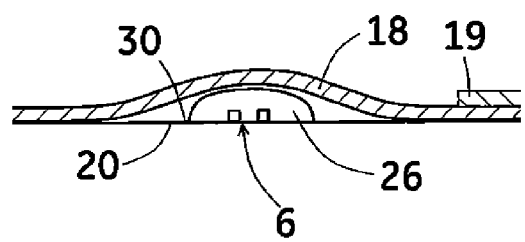
FIG. 8 is a partial view of the sensor holder of FIG. 2 showing a location for a sensor component in accordance with another embodiment.

FIG. 8 shows an alternate method of attaching the first sensor component 6 where the component is attached to the upper surface 30 of the bottom layer 20, between the bottom layer 20 and the first layer 18, after which they are encapsulated in a lens 26 from the top side. The benefit of this approach is that the bottom layer 20 does not need to be perforated and all assembly operations can be done on one side only.

Figure 9:
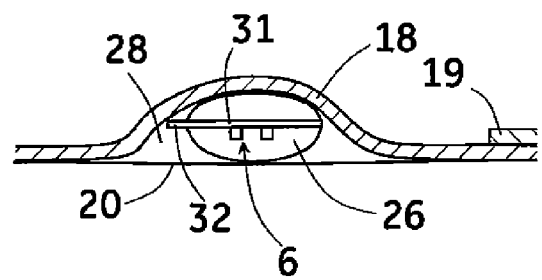
FIG. 9 is a partial view of the sensor holder of FIG. 2 showing a location for a sensor component in accordance with another embodiment.

FIG. 9 shows an assembly where the first sensor component 6 is bonded to a lead frame 31 and encapsulated, with lead fingers 32 protruding from the lens 26 allowing for wires to be soldered or welded to them. These components are then sandwiched between two layers, typically between the bottom layer 20 and the first layer 18. The layers can then be heat sealed or adhered together to form a pocket for the optics assembly.

Figure 10:
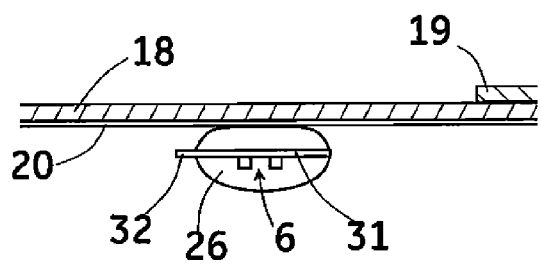
FIG. 10 is a partial view of the sensor holder of FIG. 2 showing a location for a sensor component in accordance with another embodiment.

FIG. 10 shows an assembly where the first component 6 is bonded to a lead frame 31 encapsulated, with lead fingers 32 protruding from the lens 26 allowing for wires to be soldered or welded to them. The lens 26 is then in direct contact with the application site and the first layer 18 with other layers forming the substrate acting as a spring pressing the sensor against the application site.

The embodiment introduced comprises a disposable sensor holder assembly that conforms to the site to which is it applied advantageously without the use of adhesives and can be easily repositioned without losing any of its mechanical properties. The embodiment uses elastic deformation of materials to create a desired surface pressure profile on the sensor site. This is achieved by selecting a material with suitable elastic properties to achieve the desired pressure profile.

An application area where the sensor holder described in this application would be beneficial is at least pulse oximetry ($SpO_2$), but naturally other application areas are also possible. In the pulse oximeter application the sensor typically consists of a plurality of optical emitters and a photodetector, which are located on opposing sides of an appendage. The most common application area for a $SpO_2$ sensor is the finger. As described hereinbefore, it is common for the sensor holders to cause skin symptoms as a result of prolonged use, and manufacturers therefore recommend replacing the sensor site every few hours. In accordance with the embodiments it is possible to minimize pressure necrosis and to make switching sensor site simple using a disposable $SpO_2$ sensor holder.

The proposed sensor holder provides a stable platform for the optics to allow them to align with the measurement site and provide sufficient surface pressure to help prevent motion artifacts without causing too much pressure resulting in potential pressure necrosis or other skin symptoms.

As the cross-section of a finger is typically approximately circular and the diameter of the finger may vary dramatically from person to person, designing a sensor holder that is suitable for a wide range of finger sizes can be challenging. The proposed design provides a concave sensor skin-contacting surface that conforms to a convex finger surface by means of elastic deformation. Although using a constant thickness material for this might provide a good surface pressure distribution, the pressure tends to be highest at the center of the sensor where the sensor and tissue first contact. To overcome this uneven surface pressure distribution, the present embodiment provides gradually, such as either continuously or stepwise, varying material thickness to create a more even pressure distribution. By varying the thickness so that it increases from the location of the emitter and detector components of the sensor holder outwards, a more even pressure distribution can be obtained, as show in FIG. 6. The same design can be used for both the opposite first and second substrate portions of the sensor holder, where the first sensor component, such as the emitter, and the second sensor component, such as the detector are located, and the pressure distribution can be made different for the emitter and the detector, if desired.

To achieve the static pressure on the finger, certain opposite substrate portions of the sensor holder are made convex. The material used for the substrate portions, such as sides of the sensor holder, can be the same material that is used for the surface-contacting areas. The stiffness of the substrate portions is chosen so that the desired surface pressure distribution is achieved throughout the range of finger diameters specified for use with the sensor component. When pressure is applied to the convex portions of the sensor holder, the entire sensor holder deforms elastically so that the convex portions become less convex and the skin-contacting areas become less concave as shown in FIG. 5. This increases the distance between the skin-contacting areas leaving enough space to insert the finger inside the sensor holder. When the pressure on the convex portions, which are the third and fourth substrate portions, is released, the sensor holder strives to return to its original shape, applying pressure on the skin-contacting areas pressing them against the skin as shown in FIG. 6.

If the longitudinal stiffness of the sensor holder along the longitudinal axis 10 of the hollow 5, which is an orientation perpendicular to the cross-section shown in FIG. 3, is constant or close to constant, the proposed design also provides a force that strives to align the sensor holder with the finger. If the sensor holder is applied to the finger at an angle, the pressure distribution will be uneven causing the sensor holder to rotate and align with the finger. This makes the sensor holder easier to apply properly and helps to achieve a good signal after frequent sensor holder site switches.

In addition to $SpO_2$ sensors, the sensor holder can be used to hold a variety of other sensors, such as temperature sensors, heart rate sensors, skin impedance sensors etc. The disposable sensor holder of the present embodiment provides a stable, easily repositionable platform for any application where a sensor needs to be applied to the skin of a person.

The written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A sensor holder to be applied on an appendage of a subject, said sensor holder comprising:
    a substrate comprising a first concave substrate portion, the first concave substrate portion comprising a first location configured to receive a first sensor component, the substrate surrounding a hollow for receiving the appendage along a longitudinal axis of said hollow;
    wherein the first concave substrate portion comprises a stepwise or continuous increase in thickness when drawing away from the first location along a direction of the substrate that is perpendicular to the longitudinal axis of the hollow.

2. The sensor holder according to claim 1, wherein the substrate comprises a closed loop cross section, the substrate comprising a second concave substrate portion opposite the first concave substrate portion, the second concave substrate portion comprising a second location configured to receive a second sensor component, one of the first sensor component and the second sensor component comprising at least one emitter configured to emit radiation through the appendage and another of the first sensor component and the second sensor component comprising at least one detector for receiving the radiation.

3. The sensor holder according to claim 1, wherein the substrate further comprises a second concave substrate portion opposite the first concave substrate portion, the second concave substrate portion having a second location configured to receive a second sensor component, and
    wherein the second concave substrate portion is configured to stepwise or continually increase in thickness when drawing away from the second location along the direction of the substrate that is perpendicular to the longitudinal axis of the hollow.

4. The sensor holder according to claim 3, wherein the substrate further comprises a third substrate portion and a fourth substrate portion between the first concave substrate portion and the second concave substrate portion, the third substrate portion and the fourth substrate portion being opposite each other.

5. The sensor holder according to claim 4, wherein the thickness of the third substrate portion and the fourth substrate portion is uniform.

6. The sensor holder according to claim 4, wherein the third substrate portion and the fourth substrate portion are convex in shape.

7. The sensor holder according to claim 1, wherein the first location is encapsulated to form a lens.

8. The sensor holder according to claim 1, wherein the substrate comprises a bottom layer surrounding the hollow, the first location being on one side of the bottom layer.

9. The sensor holder according to claim 1, wherein the first location is inside the substrate.

10. A sensor holder to be applied on an appendage of a subject, said sensor holder comprising:
    a substrate comprising a first concave substrate portion, a second concave substrate portion, a third substrate portion, and a fourth substrate portion,
        wherein the first concave substrate portion is disposed opposite to the second concave substrate portion, the third substrate portion disposed opposite to the fourth substrate portion, and the third substrate portion and fourth substrate portion connecting the first concave substrate portion with the second concave substrate portion,
        wherein the first concave substrate portion comprises a first location configured to receive a first sensor component configured to emit radiation, the second concave substrate portion comprising a second location configured to receive a second sensor component, the second sensor component configured to receive the radiation emitted by said first sensor component,
        wherein the substrate surrounds a hollow for receiving the appendage along a longitudinal axis of said hollow,
        wherein the first concave substrate portion comprises a stepwise or continuous increase in thickness when drawing away from the first location toward the third substrate portion and toward the fourth substrate portion, such that the increase in thickness is configured to occur along a direction of the substrate that is perpendicular to the longitudinal axis of the hollow, and
        wherein the second concave substrate portion is configured to stepwise or continuously increase in thickness when drawing away from the second location toward the third substrate portion and toward the fourth substrate portion, such that the increase in thickness is configured to occur along the direction of the substrate that is perpendicular to the longitudinal axis of the hollow.

11. The sensor holder according to claim 10, wherein a thickness of the third substrate portion and fourth substrate portion is uniform.

12. The sensor holder according to claim 10, wherein the third substrate portion and the fourth substrate portion are convex in shape.

13. The sensor holder according to claim 10, wherein the substrate is configured to form a closed loop.

14. The sensor holder according to claim 10, wherein:
    the first concave substrate portion comprises a first layer on top of a bottom layer, and a second layer on top of the first layer,
    wherein the first layer is disposed a predetermined distance from and extends away from the first location toward the third substrate portion and toward the fourth substrate portion, and
    wherein the second layer is disposed a predetermined distance from and extends away from the first location, the predetermined distance of the second layer being further toward the third substrate portion and further toward the fourth substrate portion than the first layer, wherein the second layer disposed on top of the first layer is configured to form the stepwise increasing thickness of the substrate.

15. The sensor holder according to claim 14, wherein:

the second concave substrate portion comprises a bottom layer bordering the hollow, a first layer on top of the bottom layer, and a second layer on top of the first layer, wherein the first layer is disposed a predetermined distance from and extends away from the second location toward the third substrate portion and toward the fourth substrate portion, and wherein the second layer is disposed a predetermined distance from and extends away from the second location, the predetermined distance of the second layer being further toward the third substrate portion and further toward the fourth substrate portion than the first layer, wherein the second layer disposed on top of the first layer is configured to form the stepwise increasing thickness of the substrate.

16. The sensor holder according to claim 14, wherein the substrate further comprises a bottom layer below the first layer and extending along the hollow.

17. The sensor holder according to claim 16, wherein the first location is on one side of the bottom layer.

18. The sensor holder according to claim 16, wherein the first location comprising the first sensor component is on an upper surface of the bottom layer and is between the bottom layer and the first layer.

19. The sensor holder according to claim 10, wherein the first location is encapsulated to form a lens.

20. The sensor holder according to claim 10, wherein said the first location comprising the first sensor component is inside the substrate.

* * * * *